(12) United States Patent
Klein

(10) Patent No.: US 7,670,385 B2
(45) Date of Patent: Mar. 2, 2010

(54) INTERNAL SOCKET AND FITTING SYSTEM FOR A PROSTHESIS

(75) Inventor: Christian Klein, Vienna (AT)

(73) Assignee: Otto Bock HealthCare GmbH, Duderstadt (DE)

( * ) Notice: Subject to any disclaimer, the term of this patent is extended or adjusted under 35 U.S.C. 154(b) by 299 days.

(21) Appl. No.: 11/746,510

(22) Filed: May 9, 2007

(65) Prior Publication Data

US 2007/0265711 A1    Nov. 15, 2007

(30) Foreign Application Priority Data

May 9, 2006    (DE)    .................... 20 2006 007 460 U

(51) Int. Cl.
*A61F 2/60* (2006.01)
(52) U.S. Cl. .............................. 623/33; 623/34; 623/25
(58) Field of Classification Search ............. 623/33–37, 623/25; 607/144, 115, 152; *A61F 2/72, A61F 2/80*
See application file for complete search history.

(56) References Cited

U.S. PATENT DOCUMENTS

| | | | |
|---|---|---|---|
| 980,457 A | 1/1911 | Toles |
| 2,424,278 A | 7/1947 | Kunkel |
| 2,464,443 A | 3/1949 | Ganoe et al. |
| 2,530,285 A | 11/1950 | Catranis |
| 2,531,074 A | 11/1950 | Miller |
| 2,533,404 A | 12/1950 | Sharp et al. |
| 2,606,325 A | 8/1952 | Nielson et al. |
| 2,664,572 A | 1/1954 | Blevens |
| 2,671,225 A | 3/1954 | Schoene et al. |
| 2,696,010 A | 12/1954 | Robinson |
| 2,696,011 A | 12/1954 | Galdik |
| 2,790,180 A | 4/1957 | Hauser |
| 2,808,593 A | 10/1957 | Andersen |
| 3,253,600 A | 5/1966 | Scholl |
| 3,309,714 A | 3/1967 | Porten |
| 3,322,873 A | 5/1967 | Hitchcock |
| 3,377,416 A | 4/1968 | Kandel |
| 3,393,407 A | 7/1968 | Kandel |
| 3,403,673 A | 10/1968 | Leod |
| 3,557,387 A | 1/1971 | Ohlenbusch |
| 3,631,542 A | 1/1972 | Potter |

(Continued)

FOREIGN PATENT DOCUMENTS

BE    675386    5/1966

(Continued)

OTHER PUBLICATIONS

International Search Report of EP 07 00 5857 mailed Oct. 12, 2007, 6 pages.

(Continued)

*Primary Examiner*—Paul B Prebilic
*Assistant Examiner*—Jacqueline Woznicki
(74) *Attorney, Agent, or Firm*—Faegre & Benson LLP

(57) ABSTRACT

A fitting including an electrode assembly mounted and sealed therein. The fitting configured to be positioned within an aperture in a wall of a socket of a prosthetic apparatus. The prosthetic apparatus may include an external socket that receives and is attached to the socket as an internal socket. The electrode assembly has one or more skin contacts for conduction of myoelectrical signals to a prosthetic system. The fitting includes a groove and a retention rim to secure and seal the fitting within the aperture in the socket wall, in order to prevent the passage of air and moisture from the interior of the socket when a stump of a limb is received therein. A unidirectional valve provides for the release of air from the interior of the socket.

18 Claims, 6 Drawing Sheets

U.S. PATENT DOCUMENTS

| | | | |
|---|---|---|---|
| 3,712,298 A | 1/1973 | Snowdon et al. | |
| 3,732,578 A | 5/1973 | Pollack | |
| 3,751,733 A | 8/1973 | Fletcher et al. | |
| 3,858,379 A | 1/1975 | Graves et al. | |
| 3,895,405 A | 7/1975 | Edwards | |
| 3,975,350 A | 8/1976 | Hudgin et al. | |
| 3,991,424 A | 11/1976 | Prahl | |
| 4,029,087 A | 6/1977 | Dye et al. | |
| 4,077,402 A | 3/1978 | Bengamin, Jr. et al. | |
| 4,215,679 A | 8/1980 | Rustin | |
| 4,283,800 A | 8/1981 | Wilson | |
| 4,314,398 A | 2/1982 | Pettersson | |
| 4,381,768 A | 5/1983 | Erichsen et al. | |
| 4,387,472 A | 6/1983 | Wilson | |
| 4,404,296 A | 9/1983 | Schapel | |
| 4,456,642 A | 6/1984 | Burgdorfer et al. | |
| 4,466,936 A | 8/1984 | Schapel | |
| 4,479,272 A | 10/1984 | Beldzisky | |
| 4,623,354 A | 11/1986 | Childress et al. | |
| 4,634,446 A | 1/1987 | Kristinsson | |
| 4,635,626 A | 1/1987 | Lerman | |
| 4,704,129 A | 11/1987 | Massey | |
| 4,738,249 A | 4/1988 | Linman et al. | |
| 4,743,264 A | 5/1988 | Sherva-Parker | |
| 4,822,371 A | 4/1989 | Jolly et al. | |
| 4,828,325 A | 5/1989 | Brooks | |
| 4,888,829 A | 12/1989 | Kleinerman | |
| 4,908,037 A | 3/1990 | Ross | |
| 4,922,893 A | 5/1990 | Wright et al. | |
| 4,923,475 A | 5/1990 | Gosthnian et al. | |
| 5,007,937 A * | 4/1991 | Fishman et al. | 623/34 |
| 5,025,781 A | 6/1991 | Ferrari | |
| 5,108,455 A | 4/1992 | Telikicherla | |
| 5,133,776 A | 7/1992 | Crowder | |
| 5,139,523 A * | 8/1992 | Paton et al. | 623/37 |
| 5,163,965 A | 11/1992 | Rasmusson et al. | |
| 5,186,163 A | 2/1993 | Dye | |
| 5,211,667 A | 5/1993 | Danforth | |
| 5,218,954 A | 6/1993 | van Bemmelen | |
| 5,221,222 A | 6/1993 | Townes | |
| 5,253,656 A | 10/1993 | Rincoe et al. | |
| 5,258,037 A * | 11/1993 | Caspers | 623/36 |
| 5,314,497 A | 5/1994 | Fay et al. | |
| 5,362,834 A | 11/1994 | Schapel et al. | |
| 5,376,129 A | 12/1994 | Faulkner et al. | |
| 5,376,131 A | 12/1994 | Lenze et al. | |
| 5,376,132 A | 12/1994 | Caspers | |
| 5,383,894 A | 1/1995 | Dye et al. | |
| 5,397,628 A | 3/1995 | Crawley et al. | |
| 5,413,611 A * | 5/1995 | Haslam et al. | 623/25 |
| 5,443,525 A * | 8/1995 | Laghi | 623/25 |
| 5,464,443 A | 11/1995 | Wilson et al. | |
| 5,480,455 A | 1/1996 | Norvell | |
| 5,507,834 A | 4/1996 | Laghi | |
| 5,514,186 A | 5/1996 | Phillips | |
| 5,534,034 A | 7/1996 | Caspers | |
| 5,549,709 A | 8/1996 | Caspers | |
| 5,571,208 A * | 11/1996 | Caspers | 623/32 |
| 5,593,454 A | 1/1997 | Helmy | |
| 5,658,353 A * | 8/1997 | Layton | 623/34 |
| 5,658,354 A | 8/1997 | Norvell | |
| 5,662,715 A | 9/1997 | Slemker | |
| 5,674,262 A | 10/1997 | Tumey | |
| 5,702,489 A * | 12/1997 | Slemker | 623/34 |
| 5,728,167 A | 3/1998 | Lohmann | |
| 5,728,168 A | 3/1998 | Laghi et al. | |
| 5,728,169 A | 3/1998 | Norvell | |
| 5,728,170 A | 3/1998 | Becker et al. | |
| 5,735,906 A | 4/1998 | Caspers | |
| 5,830,237 A | 11/1998 | Kania | |
| 5,888,216 A | 3/1999 | Haberman | |
| 5,888,230 A | 3/1999 | Helmy | |
| 5,888,231 A | 3/1999 | Sandvig et al. | |
| 5,904,721 A | 5/1999 | Henry et al. | |
| 5,904,722 A | 5/1999 | Caspers | |
| 5,935,146 A | 8/1999 | McEwen et al. | |
| 5,968,073 A | 10/1999 | Jacobs | |
| 5,980,577 A * | 11/1999 | Radis et al. | 623/36 |
| 6,007,559 A | 12/1999 | Arkans | |
| 6,063,125 A | 5/2000 | Arbogast et al. | |
| D429,335 S | 8/2000 | Caspers et al. | |
| 6,106,559 A | 8/2000 | Meyer | |
| 6,117,177 A | 9/2000 | Chen et al. | |
| 6,231,532 B1 | 5/2001 | Watson et al. | |
| 6,231,616 B1 * | 5/2001 | Helmy | 623/34 |
| 6,231,617 B1 | 5/2001 | Fay | |
| 6,273,918 B1 | 8/2001 | Yuhasz et al. | |
| 6,287,345 B1 | 9/2001 | Slemker et al. | |
| 6,290,662 B1 | 9/2001 | Morris et al. | |
| 6,358,453 B1 | 3/2002 | Slemker et al. | |
| 6,368,357 B1 | 4/2002 | Schon et al. | |
| 6,387,065 B1 | 5/2002 | Tumey | |
| 6,423,017 B2 | 7/2002 | Brotz | |
| 6,494,852 B1 | 12/2002 | Barak et al. | |
| 6,500,210 B1 | 12/2002 | Sabolich et al. | |
| 6,508,842 B1 | 1/2003 | Caspers | |
| 6,544,202 B2 | 4/2003 | McEwen et al. | |
| 6,554,868 B1 | 4/2003 | Caspers | |
| 6,585,774 B2 | 7/2003 | Dean, Jr. et al. | |
| 6,645,253 B2 | 11/2003 | Caspers | |
| 6,673,117 B1 | 1/2004 | Soss et al. | |
| 6,726,726 B2 | 4/2004 | Caspers | |
| 6,761,742 B2 | 7/2004 | Caspers | |
| 6,926,742 B2 | 8/2005 | Caspers et al. | |
| 6,974,484 B2 | 12/2005 | Caspers | |
| 7,025,792 B2 | 4/2006 | Collier | |
| 7,025,793 B2 * | 4/2006 | Egilsson | 623/36 |
| 7,150,762 B2 | 12/2006 | Caspers | |
| 2001/0005798 A1 | 6/2001 | Caspers | |
| 2001/0016781 A1 | 8/2001 | Caspers | |
| 2002/0091449 A1 | 7/2002 | Caspers et al. | |
| 2004/0024322 A1 | 2/2004 | Caspers | |
| 2004/0030411 A1 | 2/2004 | Caspers | |
| 2004/0059432 A1 | 3/2004 | Janusson et al. | |
| 2004/0098136 A1 | 5/2004 | Caspers | |
| 2004/0143345 A1 | 7/2004 | Caspers | |
| 2004/0163278 A1 | 8/2004 | Caspers | |
| 2004/0167638 A1 | 8/2004 | Caspers | |
| 2004/0181290 A1 | 9/2004 | Caspers | |
| 2004/0260402 A1 * | 12/2004 | Baldini et al. | 623/33 |
| 2004/0260403 A1 * | 12/2004 | Patterson et al. | 623/34 |
| 2006/0282174 A1 * | 12/2006 | Haines | 623/24 |
| 2007/0055383 A1 * | 3/2007 | King | 623/34 |
| 2007/0191965 A1 * | 8/2007 | Colvin et al. | 623/34 |

FOREIGN PATENT DOCUMENTS

| | | |
|---|---|---|
| DE | 0745981 | 5/1944 |
| DE | 1 566 408 | 2/1971 |
| DE | 2712342 | 9/1977 |
| DE | 2729800 | 1/1979 |
| DE | 3221920 | 4/1983 |
| DE | 4039648 | 7/1992 |
| DE | 4217877 | 12/1992 |
| DE | 4321182 | 12/1994 |
| DE | 9418210 | 3/1995 |
| DE | 9419211 | 3/1995 |
| DE | 9417913 | 4/1995 |
| DE | 29905020 | 8/1999 |
| DE | 202006007460 | 9/2007 |
| EP | 0019612 | 11/1980 |
| EP | 0057839 | 8/1982 |
| EP | 0086147 | 8/1983 |
| EP | 0057838 | 3/1985 |

| | | |
|---|---|---|
| EP | 0261884 | 3/1988 |
| EP | 0320170 | 6/1989 |
| EP | 0363654 | 4/1990 |
| EP | 0631765 | 1/1995 |
| EP | 0650708 | 5/1995 |
| EP | 0870485 | 10/1998 |
| EP | 0913141 | 5/1999 |
| EP | 1857081 | 11/2007 |
| FR | 1135516 | 9/1960 |
| FR | 1532625 | 7/1968 |
| FR | 2420335 | 10/1979 |
| FR | 2501999 | 9/1982 |
| GB | 136504 | 1/1920 |
| GB | 0267988 | 3/1927 |
| GB | 267988 | 3/1927 |
| GB | 1086560 | 10/1967 |
| GB | 1 191 301 | 5/1970 |
| GB | 1 191 633 | 5/1970 |
| GB | 2069847 | 9/1981 |
| GB | 2087727 | 6/1982 |
| GB | 2149309 | 6/1985 |
| JP | 7155343 | 6/1995 |
| RU | 1771722 | 10/1992 |
| RU | 1812981 | 4/1993 |
| RU | 1812982 | 4/1993 |
| RU | 1821177 | 6/1993 |
| SU | 0425629 | 4/1974 |
| WO | WO 84/00881 | 3/1984 |
| WO | WO 95/05792 | 3/1995 |
| WO | WO 96/21405 | 7/1996 |
| WO | WO 98/04218 | 2/1998 |
| WO | WO 98/55055 | 12/1998 |
| WO | WO 99/32056 | 7/1999 |
| WO | WO 99/65434 | 12/1999 |
| WO | WO 00/03665 | 1/2000 |
| WO | WO 00/74611 | 12/2000 |
| WO | WO 01/54631 | 8/2001 |
| WO | WO 01/70147 | 9/2001 |
| WO | WO 02/065958 | 8/2002 |
| WO | WO 02/067825 | 9/2002 |
| WO | 02/085264 | 10/2002 |
| WO | WO 02/080813 | 10/2002 |
| WO | WO 03/077797 | 9/2003 |
| WO | 03/086245 | 10/2003 |
| WO | WO 03/099173 | 12/2003 |
| WO | 2005/039444 | 5/2005 |

OTHER PUBLICATIONS

"Everyone talks about the weather, but nobody does anything about it", Gore-Tex web pages from http://www.gore-tex.com/goretex/index.html, printed Jul. 3, 2001, 2 pages.

"How Do They Work? Waterproof and Breathable. Why Both?" SealSkinz Waterproof and Breathable Socks and Gloves, Web Pages from www.sealskinz.com, 4 pages.

Argenta, L.C. et al., "*Vacuum-Assisted Closure: A New Method for Wound Control and Treatment: Clinical Experience*", Annals of Plastic Surgery, vol. 38, No. 6, Jun. 1997, pp. 563-577.

Beil, Tracy L., "*Interface Pressures During Ambulation Using Suction and Vacuum-Assist Prosthetic Sockets*", A Thesis Submitted to the Graduate Faculty of St. Cloud State University, Jul. 2001.

Board, Wayne J. "*Below-knee Amputee Residual Limb Responses to Vacuum-Assisted and Suction Socket Conditions*", A Thesis Submitted to the Graduate Faculty of St. Cloud State University, Oct. 2000.

Chambers, R.B. et al., *Orthotic Management of the Neuropathic and Dysvascular Patient*, Orthotic Management of the Neuropathic and Dysvascular Patient, pp. 427-453.

Gill Bike Gear & Apparel, web pages from http://www.gillbikegear.com/page-products-baselayer.htm, printed Jul. 3, 2001, 2 pages.

Harvey, Robert M. et al., "*Research Forum—Methodology Measurements, Part II: Instrumentation and Apparatus*", Journal of Prosthethics and Orthotics, vol. 8, No. 2, 1996 (pp. 50-64).

Herrmann, L.G. et al., "*Passive Vascular Exercises*", Archives of Surgery, vol. 29, No. 5, November, pp. 697-704.

International Search Report issued in PCT/US01/09152.

International Search Report issued in PCT/US02/28700.

International Search Report issued in PCT/US03/016460.

International Search Report issued in PCT/US2001/043874.

International Search Report issued in PCT/US2001/043954.

International Search Report issued in PCT/US2001/043955.

Iwama, H. et al., "*Intermittent Pneumatic Compression on the Calf Improves Peripheral Circulation of the Leg*", Journal of Critical Care, vol. 15, No. 1, Mar. 2000, pp. 18-21.

Mak, Arthur F. T. et al., "*State-of-the-art research in lower-limb prosthetic biomechanics—socket interface*", Journal of Rehabilitation Research & Development, vol. 38, No. 2, Mar./Apr. 2001, pp. 1-16.

Morykwas, M.J. et al., "*Vacuum-Assited Closure: A new Method for Wound Control and Treatment: Animal Studies and Basic Foundation*" Annals of Plastic Surgery, vol. 38, No. 6, Jun. 1997, pp. 553-562.

Mullner, T. et al., "*The use of negative pressure to promote the healing of tissue defects: a clinical trial using the vacuum sealing technique*", British Journal of Plastic Surgery 1997, pp. 194-199.

Solomons, Organic Chemistry (6.sup.th ed,), John Wiley & Sons, Inc., New York, 1996 pp. 853-854.

Waterproof/Windproof/Breathable: How it Works, Sympa Tex Technologies GmbH Data Sheets, 5 pages.

\* cited by examiner

INTERNAL SOCKET AND FITTING SYSTEM FOR A PROSTHESIS

CROSS REFERENCE TO RELATED APPLICATION

This patent application claims priority from German Patent Application No. 20 2006 007 460.0, filed on May 9, 2006 and entitled "PROTHESENINNINSCHAFTSYSTEM", the entire contents of which are hereby expressly incorporated by reference.

TECHNICAL FIELD

This invention relates to the field of artificial prostheses for human limbs. More particularly, the present invention relates to the field of prostheses having an internal socket received and secured within an external socket.

BACKGROUND

Prosthetic elements, such as prosthetic knee joints, artificial lower legs or artificial hands are attached to prosthesis sockets, which are situated on the relevant stump of the prosthetic user. According to the desired scope or function, there is a differentiation between purely cosmetic prostheses, mechanically activated prostheses and bioelectrically controlled prostheses. The relevant extremity to be replaced, or functional element to be provided, is typically located on the exterior socket, which is attached directly to the internal socket carried on the stump.

In myoelectrically powered prostheses, the conduction of an electrical action potential from the stump musculature is necessary. These potentials are emitted by the contraction of a muscle and are measurable on the skin surface of the prosthetic wearer. The potentials collected by an electrode are amplified and sent to the control unit, which activates or deactivates the actuators. The state of the art is to equip the internal socket with a recess or aperture in which the electrode can be inserted. Between the electrode and the recess in the internal socket there is a particular gap which can lead to a relative movement between the electrode and the internal socket. Through the gap between the internal socket and the electrode, perspiration can enter the space between the internal socket and the external socket, which can affect the electrical and electronic components. This can also make cleaning the internal socket difficult.

SUMMARY OF THE INVENTION

The present invention provides an improved internal socket fitting and system in which these disadvantages do not arise. The present invention includes an internal socket which is capable of being assembled within a prosthetic external socket with accommodation features for additional prosthetic components (not shown). The internal socket has at least one recess provided for the communication of myoelectrical signals to an electrode assembly located on the internal socket. The electrode assembly is attached to and retained by a fitting received in and providing a moisture seal for the recess.

DETAILED DESCRIPTION

Figures 1, 2:
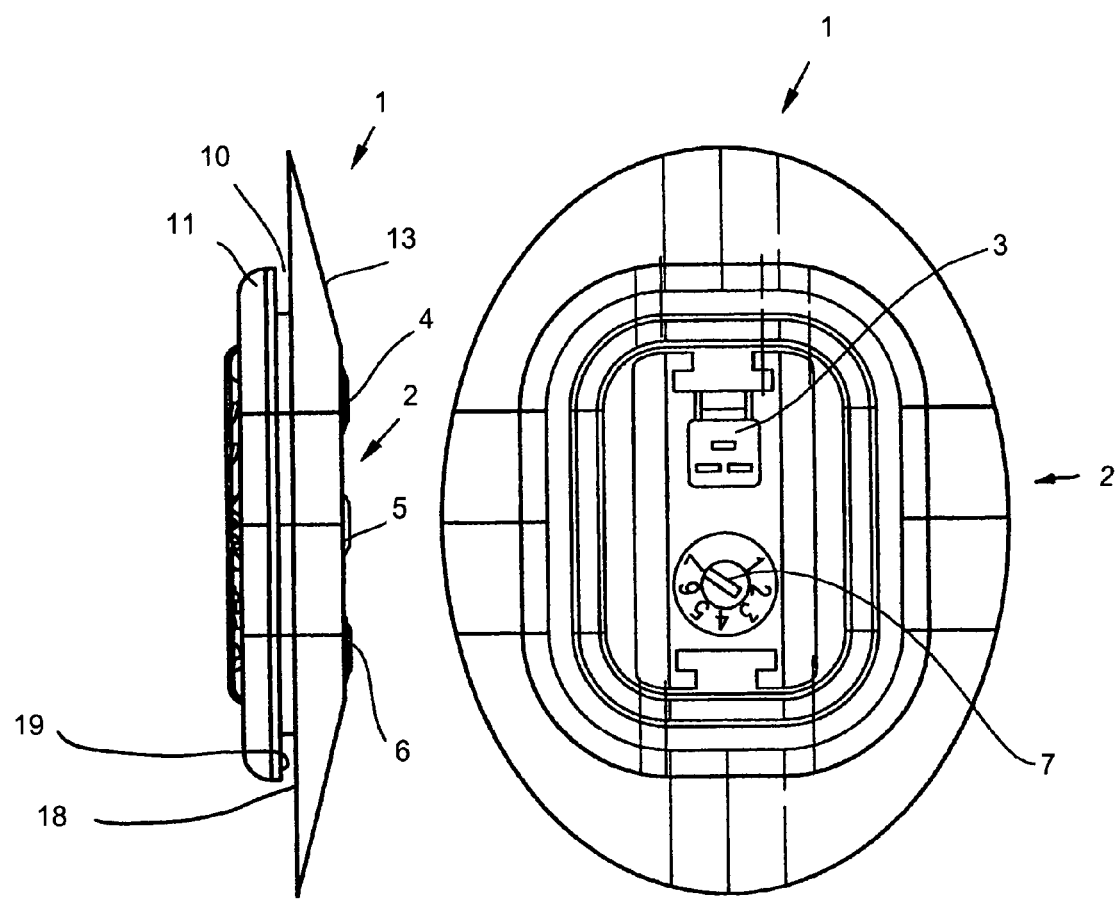
FIG. 1 shows a bottom plan view of an electrode assembly and fitting useful in the practice of the present invention.
FIG. 2 shows a side elevation view of the electrode assembly and fitting of FIG. 1.

Referring to the Figures, the present invention includes a fitting 1 carrying an electrode assembly 2, wherein the fitting is received in an internal socket 30 which is capable of being assembled within a prosthetic external socket 40 with accommodation features for additional prosthetic components (not shown).

The internal socket 30 has at least one recess or aperture 8 provided for the communication of myoelectrical signals through the electrode assembly 2 located on the internal socket 30. The electrode assembly 2 is attached to and retained by the fitting 1 received in and providing a moisture seal for the aperture 8. In one embodiment, it has been found desirable to construct the internal socket 30 as a suction socket, so that there is no gap between any of the internal socket 30, the electrode assembly 2 and the fitting 1. Air or perspiration is prevented from entering or exiting the inter-socket space 9 between an external socket 40 and the internal socket 30. Therefore any prosthesis components in the inter-socket space are protected from perspiration entering from the interior of the internal socket 30. During cleaning or when using a skin cream on the limb, material is prevented from entering the intersocket space 9 from the interior of the internal socket 30. Through airtight assembly of the fitting with the electrode assembly 2 onto the internal socket 30, at least a partial vacuum may be created, to improve contact between the stump and the electrode assembly 2 to improve the reliability of contact and therefore consistent sensing of myoelectrical signals by the electrode assembly 2.

Creation and maintenance of at least partial vacuum in the interior of the internal socket 30 also aids in (removably) securing the internal socket 30 to the stump.

Manufacture of the internal socket 30 is made easier, because it can be formed as a laminated or deep drawn structure, into which the aperture 8 may be formed or cut in accordance with the stump model in the course of manufacture.

Figure 4:
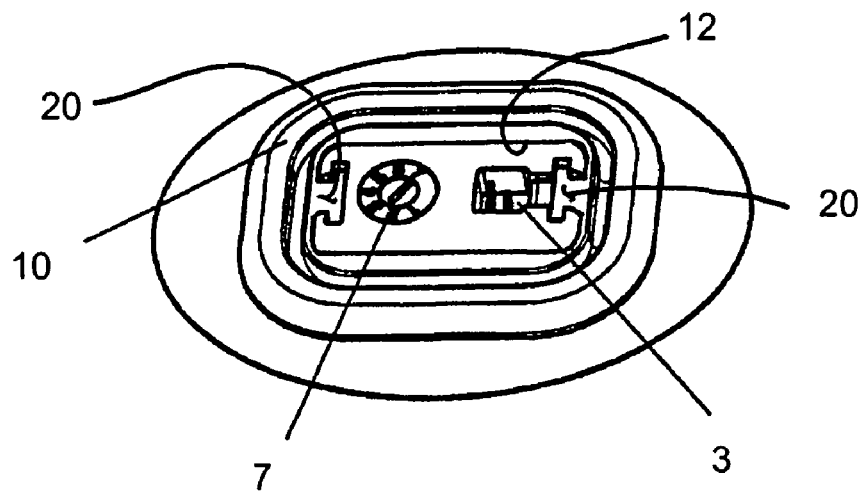
FIG. 4 shows a second perspective view from the bottom of the electrode assembly and fitting of FIG. 3.

The fitting 1 is preferably formed of an elastic or resilient material, which may be a polymer such as a silicone or other skin friendly or cutaneous tolerant material. A support structure (such as that shown as a T-shaped element 20 in FIGS. 4 and 5) for the electrode assembly 2 can be provided, as by inserting or injecting material into the fitting, for example within the framework of a two component injection method, or a support structure may be adhered, pressed or form-fit to the fitting 1, or formed integrally therewith, to result in a sealed arrangement between the fitting 1 and the electrode assembly 2. A groove 10 is preferably formed circumferentially around the fitting 1 and congruent to the aperture 8, so that the fitting 1 completely covers the internal and external edges of the aperture 8 in the internal socket 30. In this way, the aperture 8 in internal socket 30 is enclosed within two seal lips 18 and 19 which abut surfaces of the internal socket 30 when the fitting 1 is installed.

A further aspect of the present invention provides that the internal socket 30 is attached to the external socket 40 with a tube or passageway 50 onto which additional prosthesis parts may be attached. Such a passageway is preferred for insertion of the stump into the internal socket 30. A unidirectional valve 17 may be attached to the passageway 50 fluidly connected with the internal socket 30 to permit expulsion of air out of the volume between the stump and the internal socket 30 upon movement of the stump into or within the internal socket 30. The valve 17 can be located within the connection tube 50 between the internal and external sockets 30 and 40 and is operable to close the fluid passageway 50 from the internal socket 30 to the external ambient atmosphere. The design and adjustment of the valve 17 and the arrangement of the attachment tube 50 with respect to the internal socket 30 may be chosen to restrict or prevent the entrance of soft tissue into the tube 50.

It is preferred that the fitting 1 be resilient or pliable, in order to be conformable to irregularities in the stump, so that good electrical contact is provided and maintained between the electrode assembly 2 and the skin.

The top side of the fitting 1 is to be understood as the side facing toward the stump. The top side is preferably convex, and may be characterized as a flattened spherical cap. It has been found desirable that the shape of the fitting 1 with the electrode assembly 2 installed has no, or only slight, pressure points on the stump, achieved by having a low profile, i.e., only a slight projection away from the interior surface of the internal socket 30.

Fitting 1 may be inserted into the aperture 8 of the internal socket 30 by pressing or snapping into place. A curable sealant such as a curable polymer, possibly formed of silicone, may be used in the groove 10 or in the contact area between the internal socket 30 and the fitting 1 to provide a better seal.

In FIG. 1, fitting 1 is shown with electrode assembly 2 inserted. An electrical connector 3 has skin contacts 4, 5, and 6 for conduction of the action potentials of the abutting muscle groups. In the side view of FIG. 2, one form of convex construction of the top (or stump side surface) 13 of the fitting 1, along with the groove 10 and the retention rim 11 may be seen. The edge of the aperture 8 of the internal socket 30 is received in the groove 10. In one embodiment, the electrode assembly 2 may be inserted into a recess or opening 12 in the fitting 1 from the bottom side of the fitting 1 (i.e., the side of the fitting intended to face the intersocket space 9). The dimensions of the electrode assembly 2 may be greater than the corresponding dimensions of the opening 12 such that the fitting 1 is caused to extend outward, conforming the periphery of the groove 10 to the shape of the aperture 8 in the internal socket 30. Consequently, the internal and external edges of aperture 8 are urged into intimate and continuous contact within the groove 10. As a result, the region adjacent the aperture 8 in the internal socket 30 is covered by the internal side of the fitting 1, which may be configured as a flange or other structure, and the retention rim 11, and an air and watertight seal is created between the fitting 1 and the internal socket 30.

A rotary switch 7 on the back (or bottom) side of the electrode assembly 2 enables adjustment of the electrode assembly 2.

Figure 3:
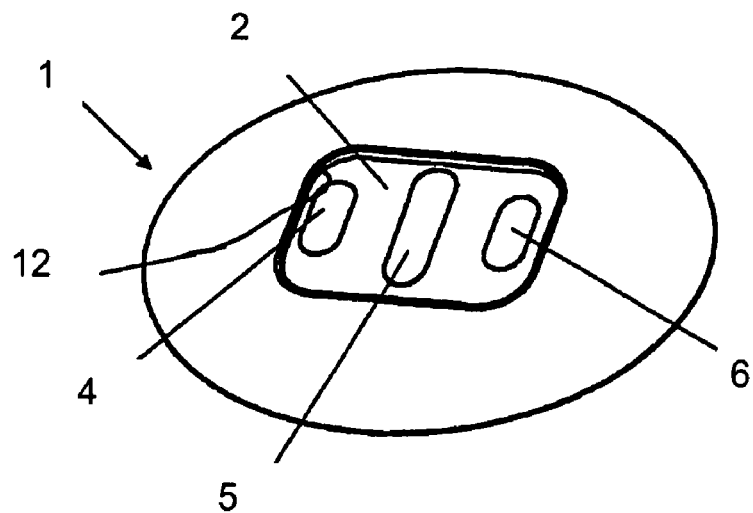
FIG. 3 shows a first perspective view from the top of the electrode assembly and fitting of FIG. 1.

The electrode assembly 2 can be injected, adhered, pressed or form-fit into the fitting 1. In the perspective views of FIGS. 3 & 4, one can see the finished mounted electrode assembly 2 in fitting 1.

Figure 5:
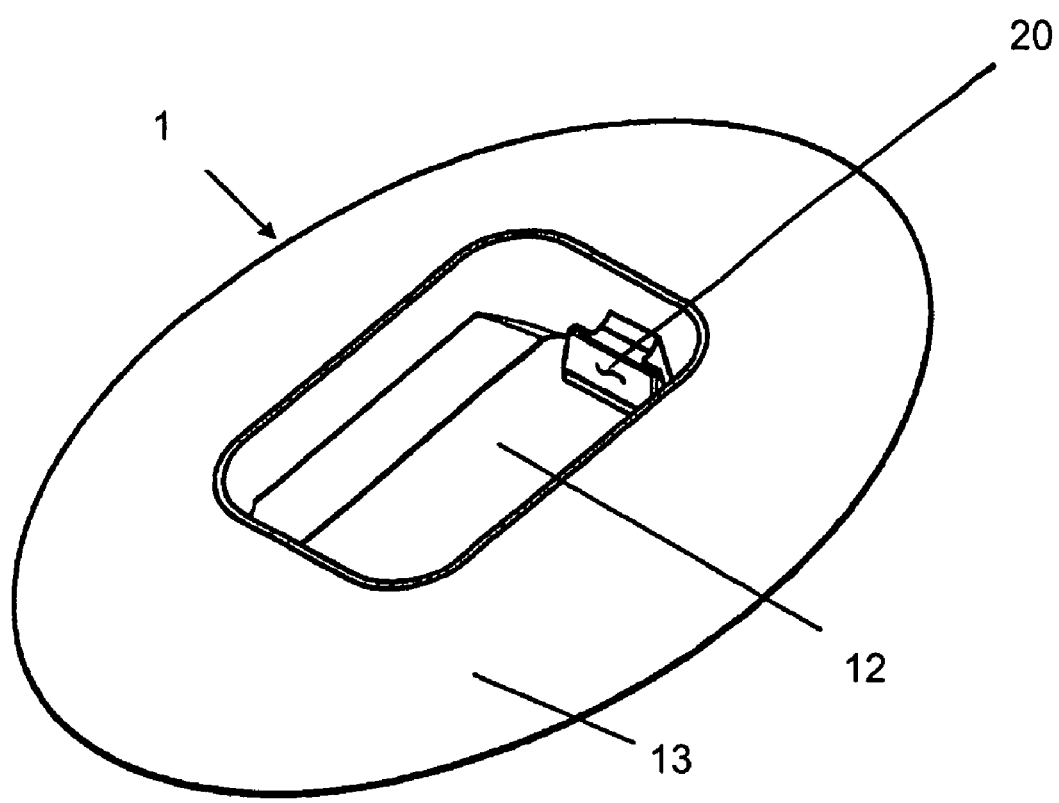
FIG. 5 shows a perspective view from the top of the fitting without the electrode assembly.
Figure 6:
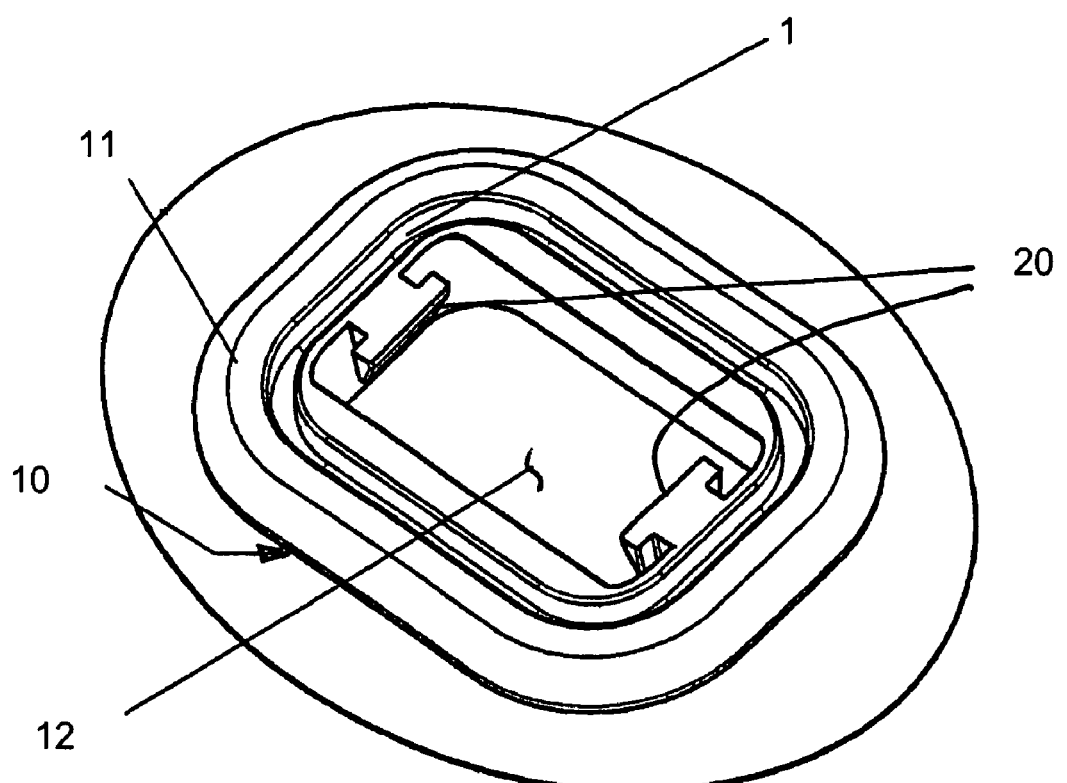
FIG. 6 shows a perspective view from the bottom of the fitting of FIG. 5 without the electrode assembly.

With a design having the electrode assembly 2 initially separate from the fitting 1, the fitting 1, as shown in FIGS. 5 and 6 in various views, may be made as a molded part or injection molded part of a skin tolerable material, such as a polymer, for example, silicone. The fitting 1 may be equipped with opening 12 for the insertion of the electrode assembly 2.

Figure 7:
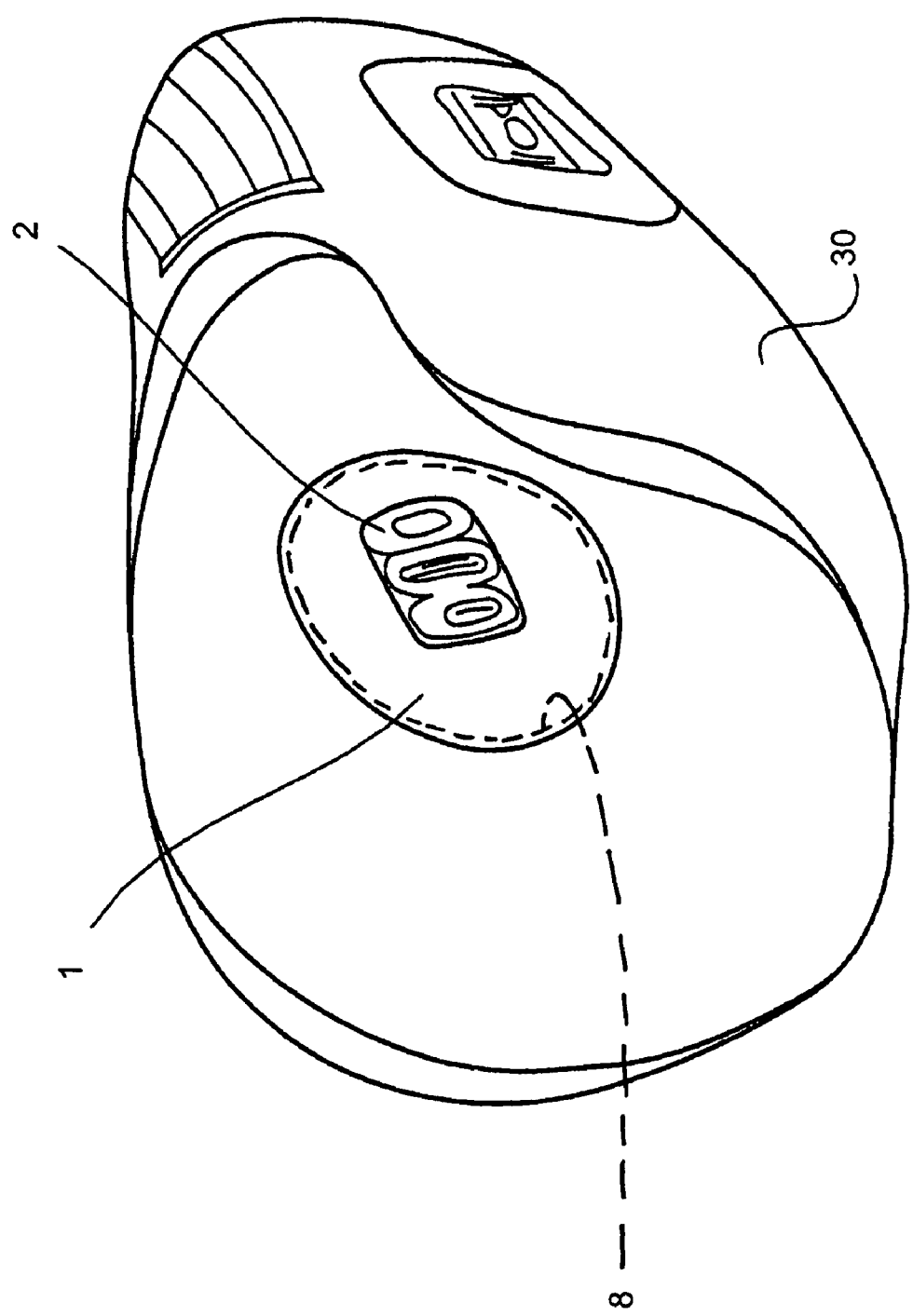
FIG. 7 shows a perspective view of an internal socket from a proximal end of the socket with the electrode assembly and fitting installed therein.

In FIG. 7, the internal socket 30 is represented diagonally from the back or proximal end, i.e., from the insertion direction of the stump, an arm stump for example. The internal socket 30 may be constructed as a suction socket. In this view, the electrode assembly 2 may be seen inside the internal socket 30. The contour of the fitting 1 on the internal side of socket 30 is preferably only slightly convex, in order to provide the most comfortable feeling for the wearer without pressure points. This also provides a secure connection between the skin contacts 4, 5, 6 and the stump, so that there is a reliable electro-myographic signal path established and maintained. As described above, the fitting 1 is equipped with groove 10, which is sealed to the internal socket 30, to prevent entry of air or moisture from the internal side of socket 30 into the intersocket space 9.

Figure 8:
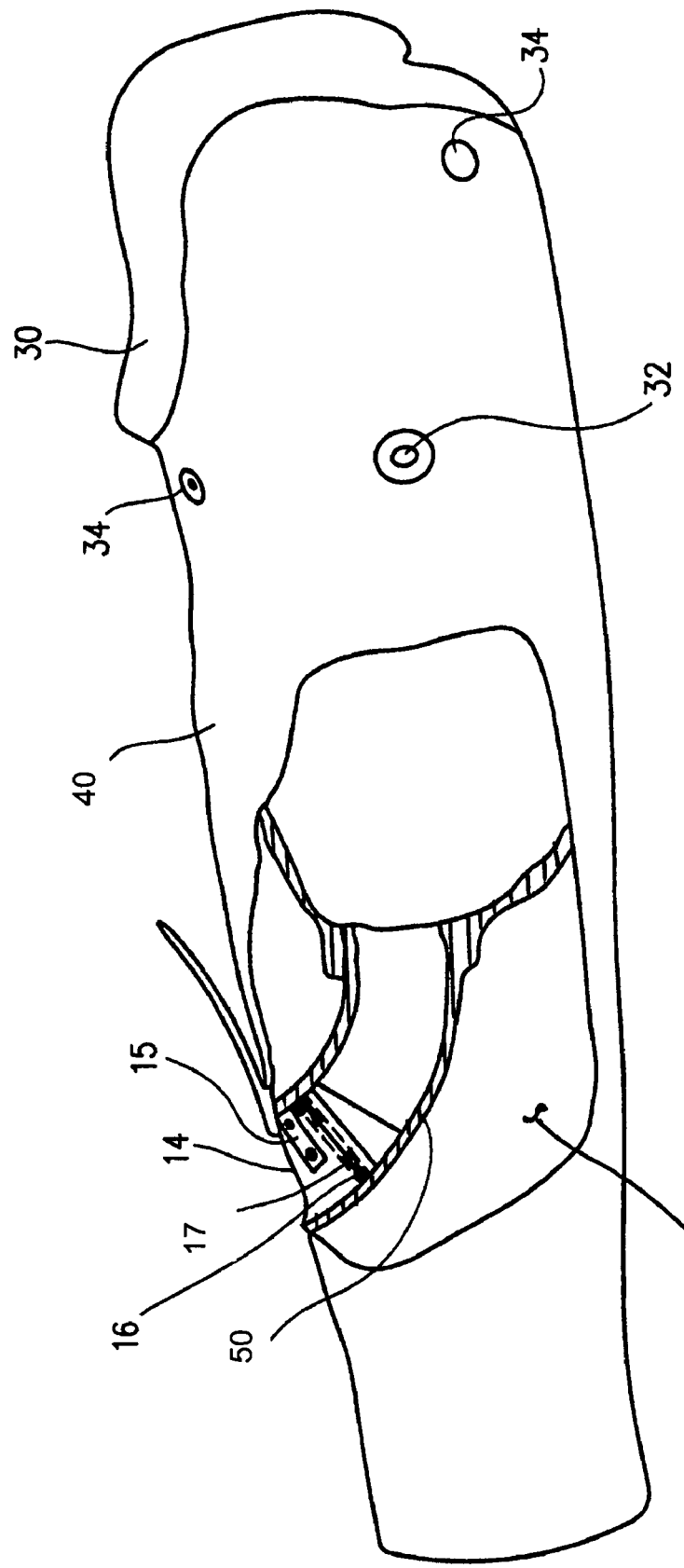
FIG. 8 shows a side view of an assembly of an external socket and internal socket with portions of each cut away to illustrate certain aspects of the present invention.

In FIG. 8, a prosthesis apparatus may be seen with an internal socket 30, and an external socket 40, with each of the internal and external sockets 30, 40 shown in a partially cutaway representation. The internal socket 30 may be secured via screws 34 to the exterior socket 40. In addition, an access hole 32 may be provided in the external socket 40, through which the electrode assembly 2 (attached to internal socket 30), can be adjusted by manipulation of rotational switch 7. The periphery of access hole 32 may be sealed against the entry of moisture and other contaminants from the external ambient environment, if desired.

In the partial cutaway representation of FIG. 8, the internal socket 30 is attached to the external socket 40 or exterior of the external socket 40 via a connection tube or passageway 50. The connection tube 50 enables escape of the air in the internal socket 30 to an appropriate location in the external socket 40 or to the external ambient environment. In order to prevent back flow of air, a unidirectional valve 17 is located in the connection tube 50. Through use of a lever 15, an O-ring 16 is activated within the connection tube 50 and thereby seals off the internal socket 30. Air can then only escape through he unidirectional valve 17.

The invention is not to be taken as limited to all of the details thereof as modifications and variations thereof may be made without departing from the spirit or scope of the invention.

The invention claimed is:

1. A prosthetic apparatus comprising:
    a socket for receiving a stump of a limb, the socket including an aperture in a wall of the socket;
    a fitting positioned within the aperture and supported by the socket, the fitting including a flange and a retention rim forming a groove that is sized to attach and seal the fitting within the aperture in the socket wall, the flange and the retention rim covering an internal edge and an external edge, respectively, of the aperture in the socket wall; and
    an electrode assembly for the conveyance of myoelectrical signals from the stump received within the socket, the electrode assembly positioned within and sealed to the fitting, such that air and moisture are prevented from passing into or out of the socket through the aperture or fitting.

2. The apparatus of claim 1 wherein the fitting is formed of an elastic material.

3. The apparatus of claim 2 wherein the material is silicone.

4. The apparatus of claim 1 wherein the electrode assembly is attached to the fitting by one or more of the methods of injection, adhesion, mechanical compression or an interference fit.

5. The apparatus of claim 1 wherein the fitting and electrode assembly together further comprise a convex cross section.

6. The apparatus of claim 5 wherein the convex cross section further comprises a flattened spherical cap that is positioned to engage the stump received within the socket.

7. The apparatus of claim 1 further comprising a connection passageway fluidly coupled to the socket.

8. The apparatus of claim 7 further comprising a unidirectional valve fluidly coupled to the connection passageway to allow air to escape from the socket.

9. The apparatus of claim 8 further comprising a vent situated within the connection passageway.

10. The apparatus of claim 8 further comprising a lever to open the valve to allow air flow into the socket.

11. The apparatus of claim 1 further comprising an external socket and wherein the socket comprises an internal socket received within and attached to the external socket.

12. The apparatus of claim 11 wherein the aperture in the internal socket wall provides an opening between an interior of the internal socket and a space between the internal socket and the external socket.

13. The apparatus of claim 12 wherein the electrode assembly comprises skin contacts on a side facing into the internal socket and electrical components on the opposite side facing into the space between the internal and external sockets.

14. The apparatus of claim 13 wherein the electrical components are accessible through a wall of the external socket.

15. A myoelectrical assembly for use with a prosthetic socket, the assembly comprising:
a fitting configured to be positioned within an aperture in a wall of the socket and to be supported by the socket, the fitting including a flange and a retention rim forming a groove that is sized to attach and seal the fitting within the aperture in the socket wall, the flange and the retention rim covering an internal edge and an external edge, respectively, of the aperture in the socket wall; and
an electrode assembly for the conveyance of myoelectrical signals from a stump received within the socket, the electrode assembly positioned within and sealed to the fitting, such that air and moisture are prevented from passing into or out of the socket through the aperture or fitting.

16. The myoelectrical assembly of claim 15 wherein the fitting is formed of an elastic material.

17. The myoelectrical assembly of claim 15 wherein the electrode assembly is attached to the fitting by one or more of the methods of injection, adhesion, mechanical compression or an interference fit.

18. A prosthetic apparatus comprising:
a socket for receiving a stump of a limb, the socket including an aperture in a wall of the socket, the socket wall surrounding the aperture including inner and outer surfaces;
a fitting positioned within the aperture and supported by the socket, the fitting including two seal lips that abut the inner and outer surfaces of the socket wall so as to seal the fitting to the socket wall; and
an electrode assembly for the conveyance of myoelectrical signals from the stump received within the socket, the electrode assembly positioned within and sealed to the fitting, such that air and moisture are prevented from passing into or out of the socket through the aperture or fitting.

* * * * *

UNITED STATES PATENT AND TRADEMARK OFFICE
CERTIFICATE OF CORRECTION

PATENT NO. : 7,670,385 B2
APPLICATION NO. : 11/746510
DATED : March 2, 2010
INVENTOR(S) : Christian Klein It is certified that error appears in the above-identified patent and that said Letters Patent is hereby corrected as shown below:

On title page item [73]
Name of Assignee should read:   Otto Bock HealthCare Products GmbH
Residence:                       Wien, Austria Signed and Sealed this Fifth Day of October, 2010

David J. Kappos
*Director of the United States Patent and Trademark Office*